United States Patent
Nakamura

(10) Patent No.: US 10,057,547 B2
(45) Date of Patent: *Aug. 21, 2018

(54) MEDICAL IMAGE RECORDING DEVICE

(71) Applicants: Shoichi Nakamura, Higashichikuma-gun, Nagano (JP); ACP JAPAN CO., LTD., Tokyo (JP)

(72) Inventor: Shoichi Nakamura, Nagano (JP)

(73) Assignees: ACP JAPAN CO., LTD., Tokyo (JP); Shoichi Nakamura, Higashichikuma-Gun, Nagano (JP)

( * ) Notice: Subject to any disclaimer, the term of this patent is extended or adjusted under 35 U.S.C. 154(b) by 208 days.

This patent is subject to a terminal disclaimer.

(21) Appl. No.: 14/892,010

(22) PCT Filed: Apr. 16, 2014

(86) PCT No.: PCT/JP2014/060771
§ 371 (c)(1),
(2) Date: Nov. 18, 2015

(87) PCT Pub. No.: WO2014/188820
PCT Pub. Date: Nov. 27, 2014

(65) Prior Publication Data
US 2016/0112680 A1    Apr. 21, 2016

(30) Foreign Application Priority Data

May 20, 2013 (JP) ................................. 2013-106011
Sep. 17, 2013 (JP) ................................. 2013-191660

(51) Int. Cl.
*H04N 7/18* (2006.01)
*G03B 5/00* (2006.01)
(Continued)

(52) U.S. Cl.
CPC ............. *H04N 7/183* (2013.01); *A61B 90/37* (2016.02); *G03B 5/00* (2013.01); *G03B 15/14* (2013.01);
(Continued)

(58) Field of Classification Search
CPC ........ A61B 90/37; G03B 15/14; G03B 17/48; G03B 2217/005; G03B 29/00; G03B 5/00;
(Continued)

(56) References Cited

U.S. PATENT DOCUMENTS 5,596,366 A * 1/1997 Takashima ........... G11B 31/006
348/208.16
2003/0053536 A1 * 3/2003 Ebrami ............ G08B 13/19634
375/240.01
(Continued)

FOREIGN PATENT DOCUMENTS

JP    S63-102378 U    7/1988
JP    2002-171469 A    6/2002
(Continued)

OTHER PUBLICATIONS

PCT, "International Search Report for International Application No. PCT/JP2014/060771".

*Primary Examiner* — Thai Tran
*Assistant Examiner* — Stephen Smith
(74) *Attorney, Agent, or Firm* — Manabu Kanesaka

(57) ABSTRACT

A medical image recording device includes an image pickup device generating an image pickup signal by photoelectrically converting light reflected from a subject with use of an image pickup element, wherein an image pickup control unit displays, on a display unit, image data generated for each of frames constituting a video by processing the image pickup signal. A recording control unit records the image data on a
(Continued)

memory card. A movement detection unit sequentially compares the image data between the adjacent frames, and calculates an amount of movement of the image pickup device from a positional shift of a main subject between the adjacent frames. If the amount of movement is within a preset range, a camera shake correction unit corrects a blur. If the amount of movement is greater than an upper limit of the range, the recording control unit stops recording of image data on the memory card.

15 Claims, 9 Drawing Sheets

(51) Int. Cl.
    *H04N 5/232*     (2006.01)
    *H04N 5/235*     (2006.01)
    *G03B 15/14*     (2006.01)
    *G03B 17/48*     (2006.01)
    *G03B 29/00*     (2006.01)
    *H04N 5/77*     (2006.01)
    *H04N 9/804*     (2006.01)
    *A61B 90/00*     (2016.01)
    *H04N 9/82*     (2006.01)
    *H04N 5/14*     (2006.01)

(52) U.S. Cl.
    CPC .............. *G03B 17/48* (2013.01); *G03B 29/00* (2013.01); *H04N 5/2328* (2013.01); *H04N 5/2354* (2013.01); *H04N 5/23254* (2013.01); *H04N 5/23258* (2013.01); *H04N 5/77* (2013.01); *H04N 9/8042* (2013.01); *G03B 2217/005* (2013.01); *H04N 5/145* (2013.01); *H04N 9/8205* (2013.01)

(58) Field of Classification Search
    CPC .............. H04N 5/145; H04N 5/23254; H04N 5/23258; H04N 5/2328; H04N 5/2354; H04N 5/77; H04N 7/183; H04N 9/8042; H04N 9/8205
    USPC ...... 386/224, 228, 248; 348/77, 143, 208.16, 348/208.1, 208.4, 208.6, 208.7; 396/52; 345/8

See application file for complete search history.

(56) References Cited

U.S. PATENT DOCUMENTS

| | | | | |
|---|---|---|---|---|
| 2004/0012713 | A1* | 1/2004 | Dittmer | A61B 1/00177 348/373 |
| 2007/0177859 | A1* | 8/2007 | Ito | G11B 19/04 396/55 |
| 2008/0136925 | A1* | 6/2008 | Azusawa | G03B 5/00 348/208.7 |
| 2009/0116830 | A1* | 5/2009 | Kumagai | G03B 13/32 396/125 |
| 2010/0053343 | A1* | 3/2010 | Kim | H04N 5/23248 348/208.4 |
| 2010/0208121 | A1* | 8/2010 | Kato | G02B 27/017 348/333.07 |
| 2011/0293244 | A1* | 12/2011 | Kuriyama | H04N 5/23245 386/248 |
| 2012/0133218 | A1* | 5/2012 | Fujii | H04M 1/72569 307/116 |
| 2012/0320236 | A1* | 12/2012 | Toyoda | H04N 5/23277 348/231.99 |
| 2013/0127980 | A1* | 5/2013 | Haddick | G06F 3/013 348/14.08 |
| 2014/0112634 | A1* | 4/2014 | Yamamoto | H04N 5/772 386/224 |
| 2014/0285677 | A1* | 9/2014 | Fujita | H04N 5/23258 348/208.6 |

FOREIGN PATENT DOCUMENTS

| | | |
|---|---|---|
| JP | 2003-032607 A | 1/2003 |
| JP | 2003-204972 A | 7/2003 |
| JP | 2005-348178 A | 12/2005 |
| JP | 2008-288829 A | 11/2008 |
| JP | 2009-077265 A | 4/2009 |
| JP | 2009-098570 A | 5/2009 |

* cited by examiner

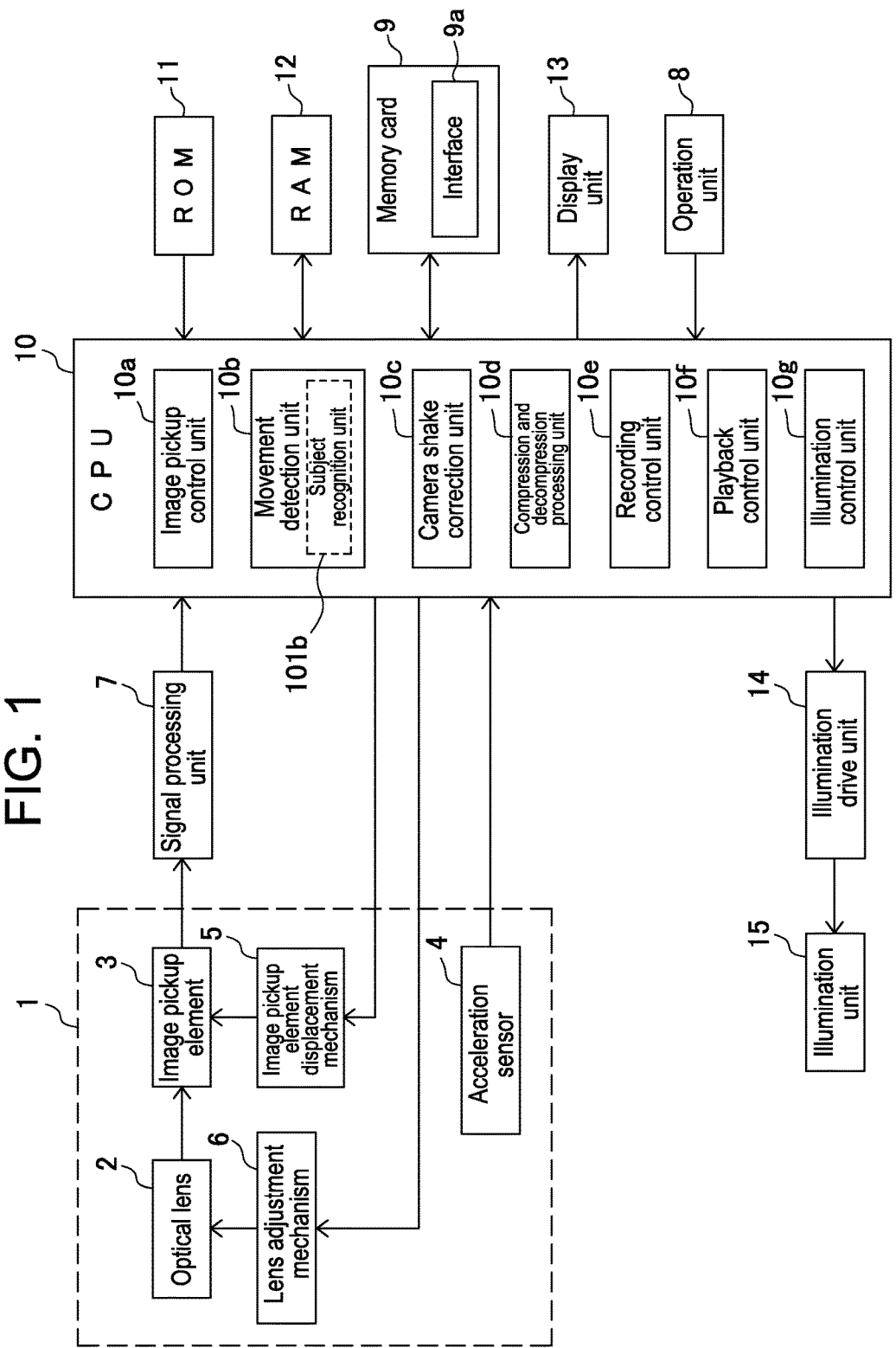

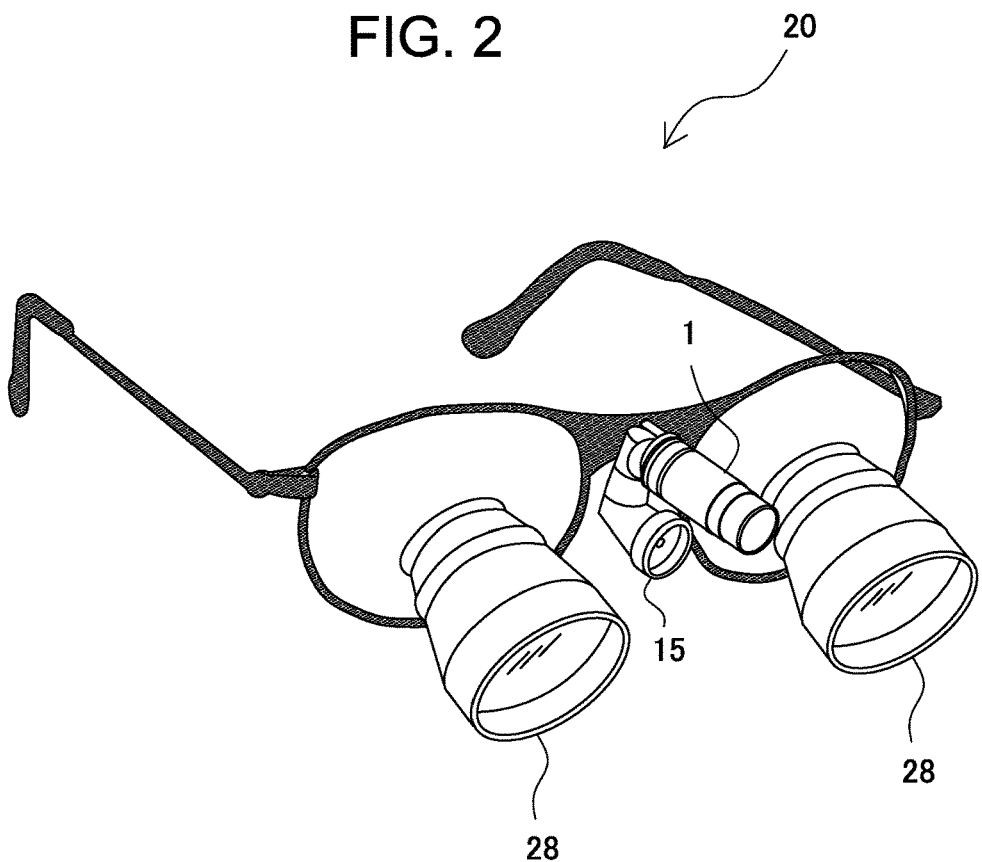
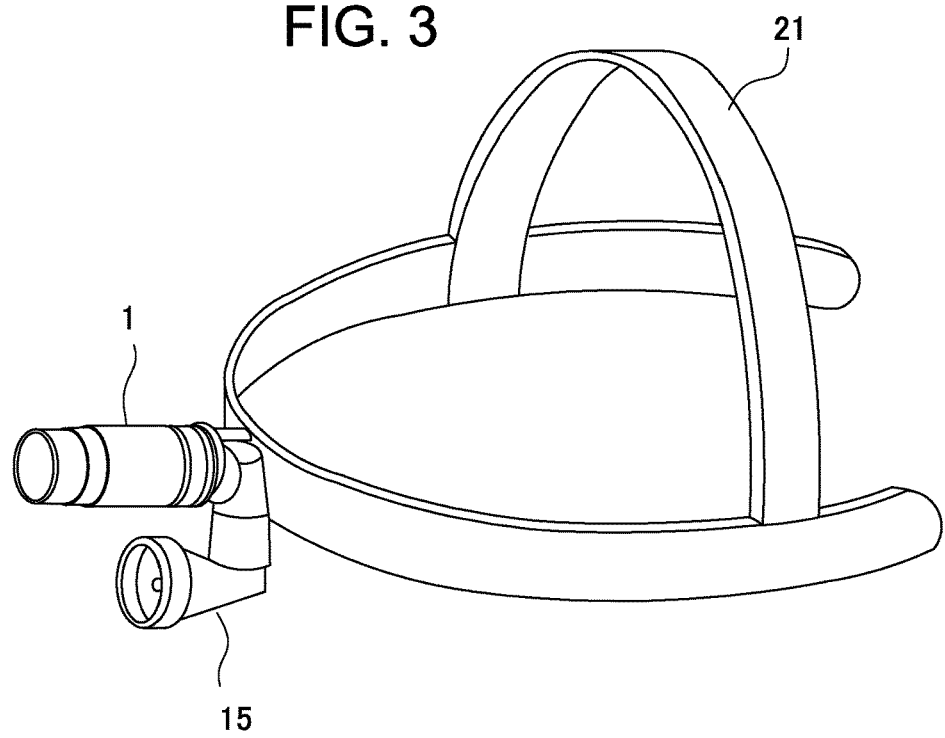

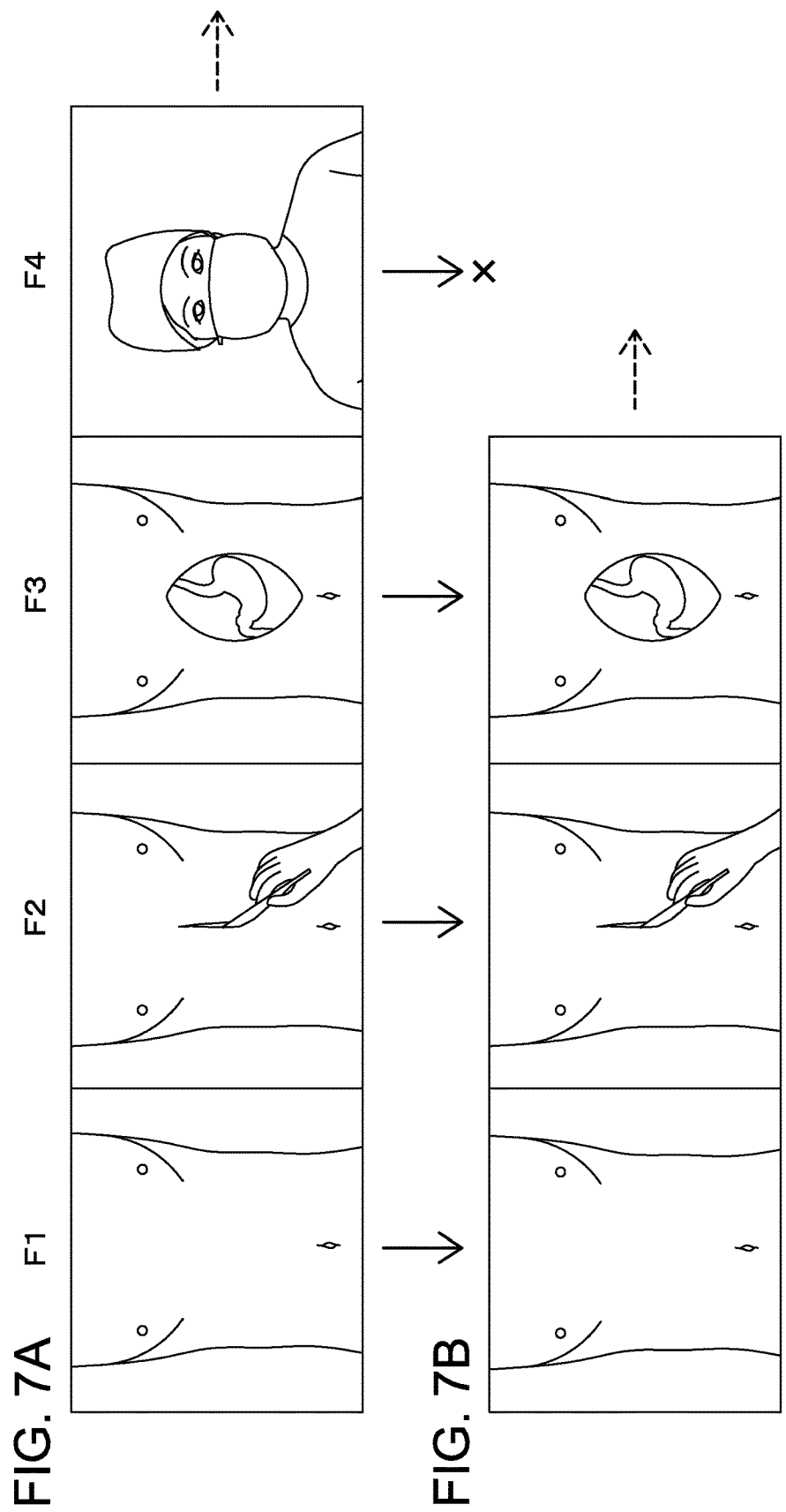

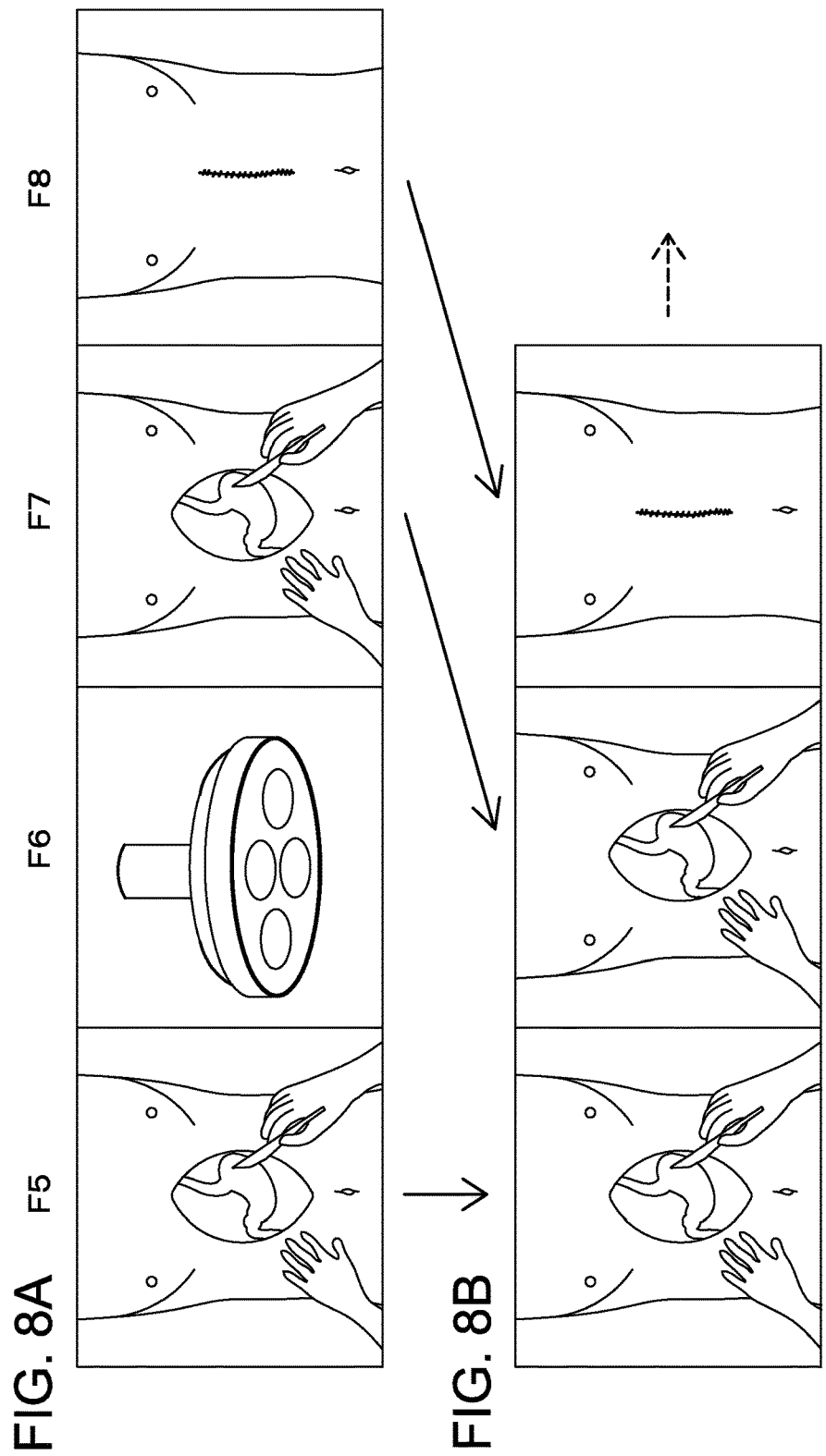

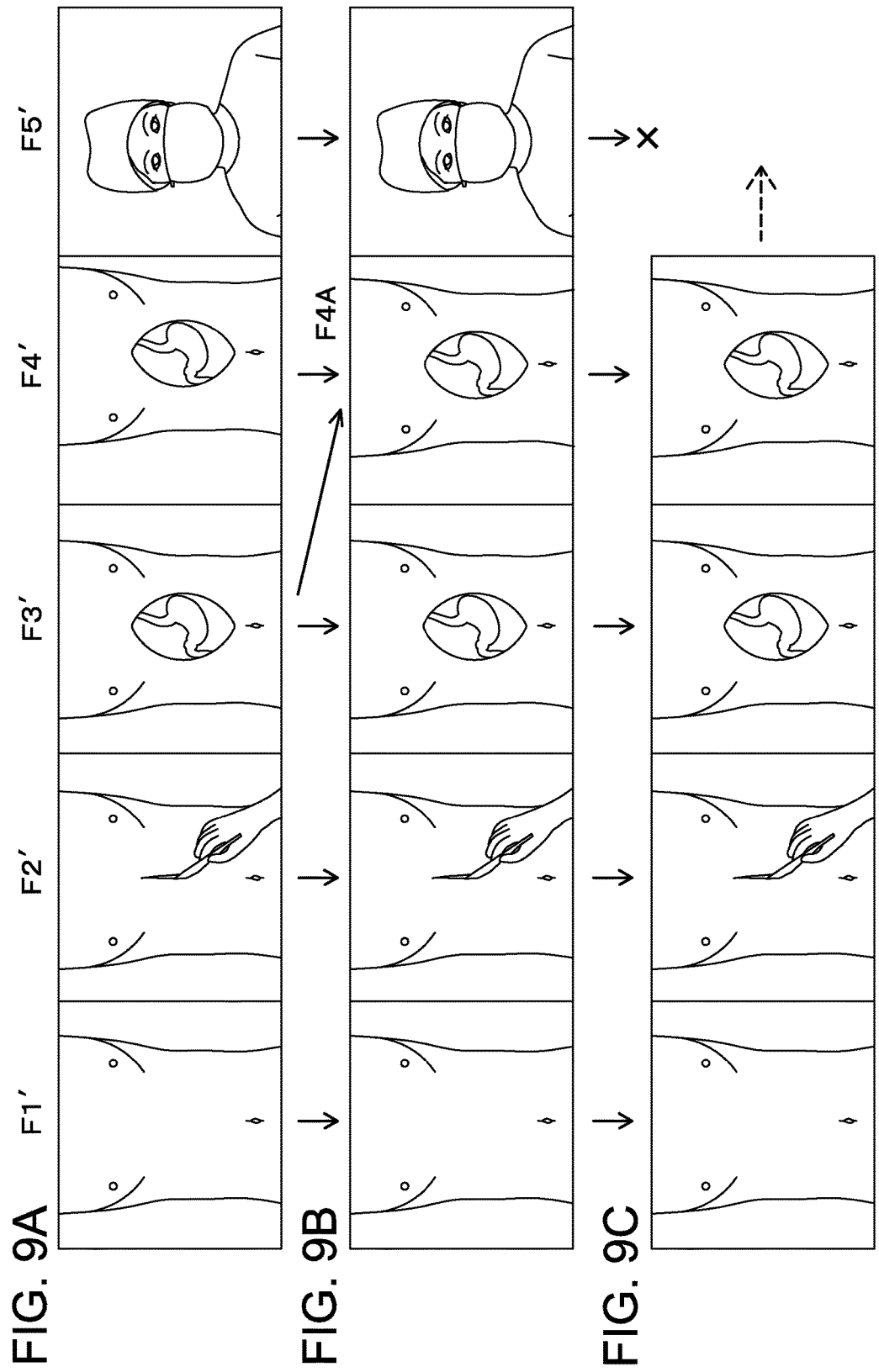

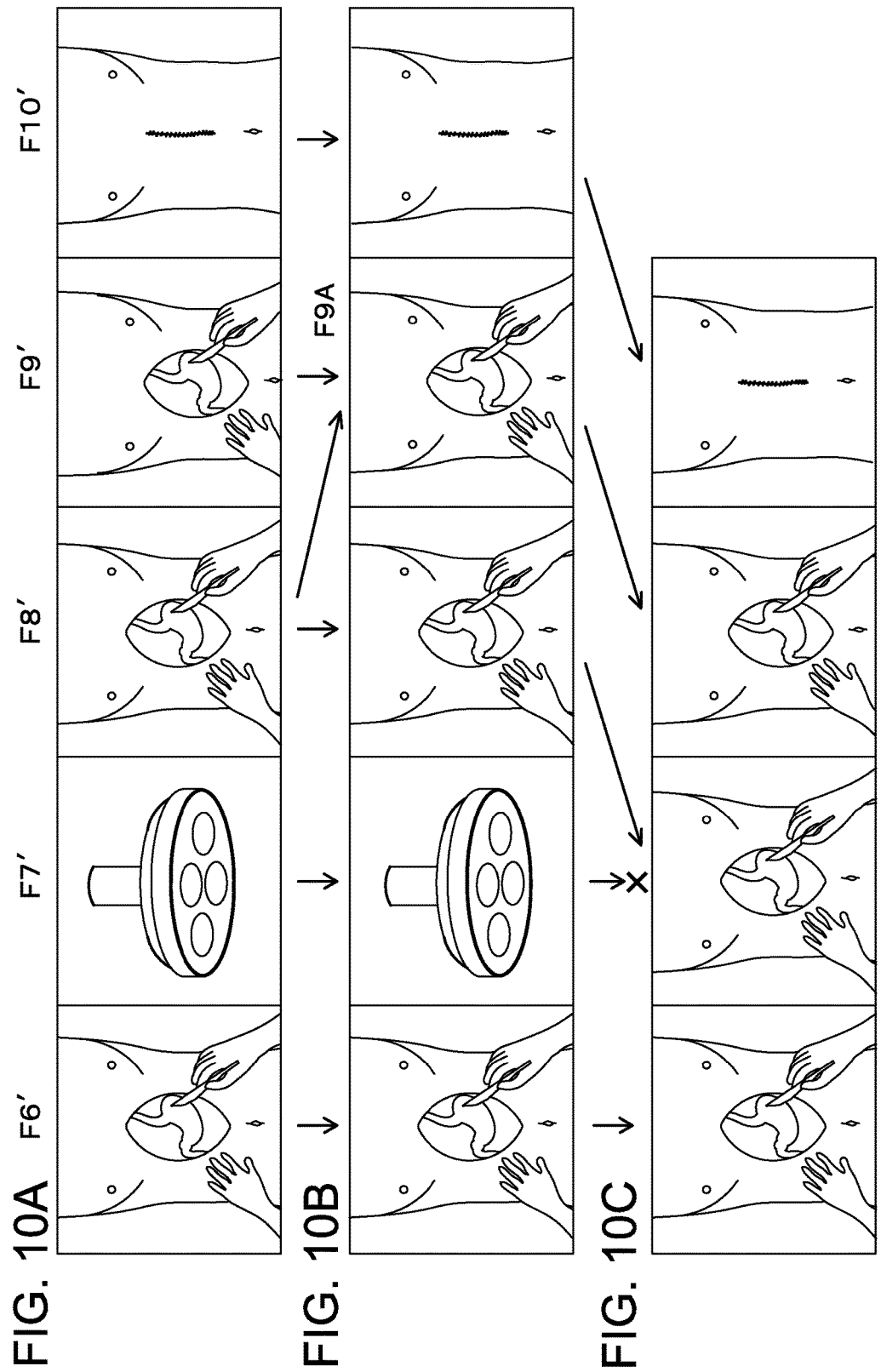

MEDICAL IMAGE RECORDING DEVICE

RELATED APPLICATIONS

The present application is National Phase of International Application No. PCT/JP2014/060771 filed Apr. 16, 2014, and claim priorities from Japanese Applications No. 2013-106011, filed May 20, 2013; and No. 2013-191660, filed Sep. 17, 2013, the disclosure of which is hereby incorporated by reference herein in its entirety.

TECHNICAL FIELD

The present invention relates to a medical image recording device that shoots pictures of treatment when medical treatment is carried out in order to record.

BACKGROUND ART

Putting an image pickup device, such as a digital video camera equipped with image pickup elements of CCD or CMOS type, on the body of an operator who carries out an operation in order to shoot a video of how the operation is going is a common practice.

In particular, in the field of medical treatment, if a video of how an operator has conducted an operation on a treatment target location is taken and left as a record, the video will be highly useful as explanatory material when a person who got the treatment or his/her family receives an explanation of how the operation is conducted after the operation, or as material for academic conferences or medical education.

In order to meet such needs, what is known is a medical image pickup device whose image pickup device is attached to a binocular loupe or headband that an operator puts on his/her head or face when conducting an operation, enabling the image pickup device to shoot a treatment target location the operator is closely watching (Refer to Patent Documents 1 and 2, for example).

However, when the image pickup device is used to shoot a subject within an image pickup range, so-called "camera shake" is a problem. The "camera shake" means that the movement of the body or head of the operator shakes the image pickup device during medical treatment, causing the video to blur. Delicate work, such as medical treatment, entails wiggling of hands. If the image pickup device that is put on the body of the operator moves when a shutter is being opened, the movement causes the video to blur, thereby making the video unclear.

In order to suppress such a camera shake, what is known is a digital camera that uses an acceleration sensor, or detects an image shift between two consecutive frames of the video, in order to obtain camera-shake information and correct the image data to correct the camera shake (Refer to Patent Document 3, for example).

PRIOR ART DOCUMENTS

Patent Documents

[Patent Document 1] Japanese Patent Application Laid-Open Publication No. 2003-204972
[Patent Document 2] Japanese Patent Application Laid-Open Publication No. 2009-98570
[Patent Document 3] Japanese Patent Application Laid-Open Publication No. 2009-77265

SUMMARY OF THE INVENTION

Problems to be Solved by the Invention

However, in the case of an image pickup recording device that leaves an image pickup result as a record, besides blurred images caused by a "camera shake" or the like, the video becomes inappropriate as a record video once a subject that should be shot and left as a record goes out of a shooting target. That is, in the case of a medical image pickup device that is put on the head or face of an operator to shoot a treatment target location that the operator is closely watching during medical treatment, for example, if the operator turns his/her face away from the treatment target location as the operator gives a treatment assistant instructions or the like during the treatment or the operator slightly moves his/her body to relax during a long medical treatment time, the image pickup device takes an image of locations other than where the treatment is carried out, and the record video becomes defective as the record video contains that image. In this case, it is annoying for the operator to operate a release switch for video shooting each time the treatment is suspended. It is also difficult for the operator to do the operation because the blood or body fluid of a patient adheres to his/her hands and fingers.

In view of the above problems, the object is to provide a medical image recording device that can save a good record video by stopping, when a shooting direction of an image pickup device is moved in such a way that an image moves away from a subject (treatment target location), recording of the captured image of a portion thereof.

Means for Solving the Problems

To solve the above problems a medical image recording device that shoots by putting, on a body of an operator conducting medical treatment, an image pickup device that includes at least an optical lens and an image pickup element which generates an image pickup signal by photoelectrically converting light introduced from a subject via the optical lens during shooting, includes: an image pickup control unit that controls in such a way as to display, on a display unit, a video from image data that is generated for each of frames that constitute the video based on the image pickup signal; an information recording unit that sequentially records the image data; a movement detection unit that sequentially compares the image data between consecutive or adjacent frames, and calculates an amount of movement of the image pickup device based on a positional shift of a main subject between the frames; a camera shake correction unit that corrects, when the amount of movement is within a preset range, a positional shift of the video caused by the movement corresponding to the amount of movement; and a recording control unit that controls stopping of the recording of the image data on the information recording unit when the amount of movement is greater than an upper limit of the range. Accordingly, it is possible to stop the recording of the image data by detecting a change in the direction of the shooting by the image pickup device through image recognition.

At this time, the image pickup control unit stops, when the amount of movement is greater than the upper limit of the range, the displaying of the video. In this case, the image pickup control unit may stop the displaying of the video after a predetermined time-lag period has passed since the movement detection unit detects that the amount of movement exceeds the upper limit of the range.

The image pickup control unit controls in such a way as to display, as a still image, the image data that appears before the movement becomes greater than or equal to the upper limit of the range, after the displaying of the video is stopped. In this case, the image pickup control unit may control in such a way as to display the still image after a predetermined time-lag period has passed since the movement detection unit detects that the amount of movement exceeds the upper limit of the range.

After the amount of movement exceeds the upper limit of the range and after a main subject detected by the movement detection unit has come to resemble the main subject that appears before the amount of movement exceeds the upper limit of the range, the recording control unit controls resumption of the recording of the image data by the information recording unit, and the image pickup control unit controls resumption of the displaying of the video.

Meanwhile, if the amount of movement is within the range, the movement is recognized as a camera shake, and the camera shake correction unit generates corrected image data by combining the image data of a plurality of consecutive or adjacent frames.

A medical image recording device of the present invention that shoots by putting, on a body of an operator conducting medical treatment, an image pickup device that includes at least an optical lens and an image pickup element which generates an image pickup signal by photoelectrically converting light introduced from a subject via the optical lens during shooting, includes: an image pickup control unit that controls in such a way as to display, on a display unit, a video from image data that is generated for each of frames that constitute the video based on the image pickup signal; an information recording unit that sequentially records the image data; an acceleration sensor that detects movement of the image pickup device; a first movement detection unit that calculates an amount of movement of the image pickup device based a detection signal of the acceleration sensor; a camera shake correction unit that controls in such a way as to cancel a blur in the video caused by the movement corresponding to the amount of movement calculated by the first movement defection unit; a second movement detection unit that sequentially compares the image data between consecutive or adjacent frames, and calculates an amount of movement of the image pickup device from a positional shift of a main subject between the frames; and a recording control unit that controls stopping of the recording of the image data when the amount of movement calculated by the second movement detection unit is greater than or equal to a preset threshold value.

Advantages of the Invention

In the medical image recording device of the present invention, when the image pickup device has captured an image that is not directly related to an operation of treatment, the image is not recorded on the recording device. Therefore, the operator does not have to turn off the shooting of the image pickup device every time. A valid record of treatment can be saved only by putting the image pickup device on the body of the operator.

BRIEF DESCRIPTION OF THE DRAWINGS

FIG. 1 is a diagram showing, as blocks, the configuration of a medical image recording device according to a first embodiment of the present invention.

FIG. 2 is an explanatory diagram of a binocular loupe that includes an image pickup device and an illumination unit.

FIG. 3 is an explanatory diagram of a head band that includes an image pickup device and an illumination unit.

FIG. 7A is an explanatory diagram schematically showing an image of each frame in a medical image recording device according to the first embodiment of the present invention; FIG. 7B is an explanatory diagram schematically showing image data recorded on a memory card.

FIG. 8A is an explanatory diagram schematically showing an image of each frame that comes after those of FIGS. 7A and 7B in a medical image recording device according to the first embodiment of the present invention; FIG. 8B is an explanatory diagram schematically showing image data recorded on a memory card.

FIG. 9A is an explanatory diagram schematically showing an image of each frame in a medical image recording device according to the second embodiment of the present invention; FIG. 9B is an explanatory diagram schematically showing image data recorded on RAM; FIG. 9C is an explanatory diagram schematically showing image data recorded on a memory card.

FIG. 10A is an explanatory diagram schematically showing an image of each frame that comes after those of FIGS. 9A-9C in a medical image recording device according to the second embodiment of the present invention; FIG. 10B is an explanatory diagram schematically showing image data recorded on RAM; FIG. 10C is an explanatory diagram schematically showing image data recorded on a memory card.

BEST MODE FOR CARRYING OUT THE INVENTION

Figure 4:
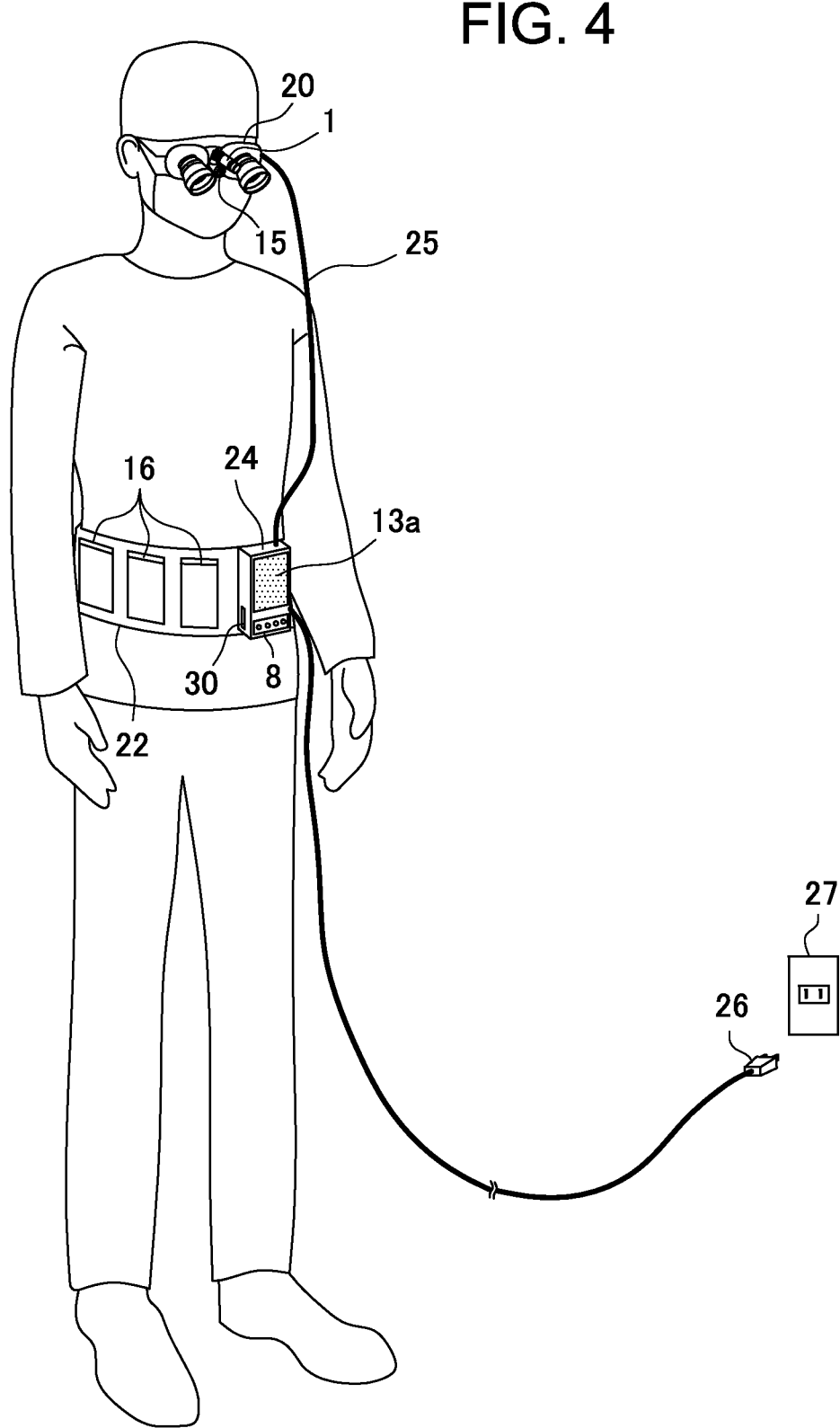
FIG. 4 is an explanatory diagram showing an example in which a medical image recording device of an embodiment of the present invention is put on an operator.

Hereinafter, optimal embodiments of the present invention will be described with reference to the accompanying drawings.

First Embodiment

FIG. 1 is a block diagram showing the schematic configuration of a medical image recording device according to a first embodiment of the present invention.

An image pickup device 1 is a digital video camera that shoots a video. The image pickup device 1 includes an optical lens 2, which allows light to enter from a subject during shooting; an image pickup element 3, which includes CCD or CMOS to generate image signals by photoelectrically converting the reflected light coming from the subject via the optical lens 2 into analog electric signals; an acceleration sensor 4; an image pickup element displacement mechanism 5; and a lens adjustment mechanism 6.

The acceleration sensor 4 detects a "camera shake". For example, a three-axis type is used. The acceleration sensor 4 detects, as acceleration, angular velocities of movements in three-axis directions of X, Y, and Z, which are perpendicular to each other with the axis of the operator's neck, as center. After carrying out such processes as A/D conversion, the acceleration sensor 4 outputs a detected signal to CPU 10.

The image pickup element displacement mechanism 5 prevents the video from blurring due to the "camera shake" by moving the image pickup element 3 based on an amount of movement of the image pickup device 1, which is calculated from acceleration detected by a movement detection unit 10b described later.

The lens adjustment mechanism 6 uses a built-in drive motor to move the optical lens 2, thereby carrying out focusing and zooming. Incidentally, although not shown in the diagram, the optical lens 2 includes a diaphragm mechanism; the aperture is adjusted by driving of the drive motor, thereby adjusting the intensity of the subject light entering the image pickup element 3.

A signal processing unit 7 amplifies an image signal that is input from the image pickup element 3, converts the image signal into a digital signal, and outputs the digital signal to the CPU 10. In the medical image recording device of the present embodiment, the video of a subject is shot at a rate of 30 frames per second, for example. Therefore, the signal processing unit 7 generates image data of each frame, and outputs the image data to the CPU 10. The function of generating image data of each frame may belong to the CPU 10.

An operation unit 8 includes a power switch, which is used to turn ON/OFF the supply of power to the image pickup device 1, a release switch, which starts the shooting of video, and a zoom switch, which is used to conduct a zooming operation of the optical lens 2.

A memory card 9, which is used as an information recording unit, records image files of the video transmitted from the CPU 10 via an interface 9a and outputs the recorded image files to the CPU 10. The image files are recorded in Motion JPEG format. The images of each frame are compressed in JPEG and successively combined. The information recording unit can use not only a memory card but also various recording media, such as various disc or memory types.

A display unit 13 includes a display panel 13a (FIG. 5), which is a liquid crystal panel or an organic EL panel. The display unit 13 displays the video shot by the image pickup device 1. The display unit 13 is also used to play and display the video of image files stored in the memory card 9.

An illumination unit 15 is used to secure the brightness of a treatment target location (subject). For example, the illumination unit 15 includes a plurality of LED elements that emit the light of each color. The illumination unit 15 is supplied with drive power from an illumination drive unit 14. In this case, it is preferred to avoid blue LED elements of a 400 nm to 500 nm band, which is said to hurt eyes.

RAM 12 is SDRAM, which is capable of high-speed reading and writing of data, for example. On the RAM 12, the image data output from the signal processing unit 7, and data being processed by the CPU are temporarily recorded.

The CPU 10 controls operation of a medical image recording device based on control programs and various setting data, which are written to the ROM 11, and how each of the various switches of the operation unit 8 is operated. By executing the control programs, the CPU 10 functions as: an image pickup control unit 10a; a movement detection unit 10b, which calculates an amount of movement of the optical lens 2 or image pickup element 3; a camera shake correction unit 10c; a compression and decompression processing unit 10d; a recording control unit 10e; a playback control unit 10f; an illumination control unit 10g; and the like.

Each control function of the CPU 10 will be described.

The image pickup control unit 10a controls, based on a switch operation of the operation unit 8, the driving of a motor contained in the lens adjustment mechanism 6 to carry out an auto focus process, a zooming process, and an exposure adjustment process, thereby controlling the shooting of a video of a subject by the image pickup device 1. The image pickup control unit 10a also performs image processing, such as white balance adjustment, color interpolation processing, and aberration correction processing, on the image data of each frame transmitted from the signal processing unit 7.

Although not shown in the diagrams, the movement detection unit 10b functions as a first movement detection unit, which detects a "camera shake" based on a detection signal supplied from the acceleration sensor 4, and as a second movement detection unit, which uses image recognition of a subject recognition unit 101b to detect that the shooting of the image pickup device 1 has shifted from the treatment target location. The subject recognition unit 101b is part of the functionality of the movement detection unit 10b, which is realized by a control program process of the CPU 10. For example, the subject recognition unit 101b may be a subroutine, function, procedure, or the like. The subject recognition unit 101b analyzes the images of image data, between consecutive or adjacent frames that the image pickup control unit 10a receives from the signal processing unit 7. Then, the subject recognition unit 101b extracts the contours of the subject as feature points, and recognizes an area where the feature points overlap; with one another as a main subject. In this case, each of images between frames that are adjacent to each other at intervals of 1/30 seconds, or each of images between frames that, are close to each other, for example, at intervals of 1/3 seconds is sequentially analyzed, and a common portion is recognized as a main subject.

The first movement detection unit of the movement detection unit 10b calculates, from acceleration components of X, Y, and Z that are output from the acceleration sensor 4, the amounts of movement of the image pickup device 1 in a left-right direction (X-direction), an up-down direction (Y-direction), and a front-back direction (Z-direction). The camera shake correction unit 10c carries out control in such a way as to correct a career a shake by operating the image pickup element displacement mechanism 5 based on the amounts of movement calculated by the first movement detection unit.

Meanwhile, the second movement detection unit of the movement detection unit 10b identifies the movement of the shooting direction of the image pickup device 1 by detecting a change of the main subject recognized by the subject recognition unit 101b. During this process, the movement detection unit 10b calculates a value of a positional shift in the vertical and horizontal directions on X-Y axes of the main subject in each of the images between frames that are adjacent to each other or in each of the images between frames that are close to each other. If the value of the positional shift calculated exceeds a preset threshold value, the movement detection unit 10b then judges that the main subject has been changed as the shooting direction of the image pickup device 1 moves away from the treatment target location, and that the treatment is suspended.

The compression and decompression processing unit 10d compresses, in JPEG, the image data of each frame loaded onto the RAM 12, thereby generating an image file of the video to be recorded on the memory card 9. When the video of an image file recorded on the memory card 9 is played, the compression and decompression processing unit 10*d* decompresses the compressed image data.

The recording control unit 10*e* controls the process of writing the image data, which has been compressed in JPEG for each frame, to the memory card 9.

The playback control unit 10*f* reads images stored in the memory card 9 to display the images on the display unit 13.

The illumination control unit 10*g* outputs a control signal to the illumination drive unit 14 in order to supply drive power to the illumination unit 15 and control the amount of current thereof.

An example of how the image pickup device 1 is put on the body of an operator will be described. In the example shown in FIG. 2, the image pickup device 1 and the illumination unit 15, which casts light on a subject, are attached to a binocular loupe 20 that an operator puts on his/her face when conducting treatment. Instead of the binocular loupe 20, a cap or a headband may be used. FIG. 3 shows a headband 21 to which the image pickup device 1 and the illumination unit 15 have been attached. The headband 21 is made of a resin member; the headband 21 is kept and fixed on the head of an operator due to the elasticity thereof. The headband 21 is not limited to this configuration. The headband 21 may be made of cloth, rubber, or the like, and can be made in various forms.

Figure 5:
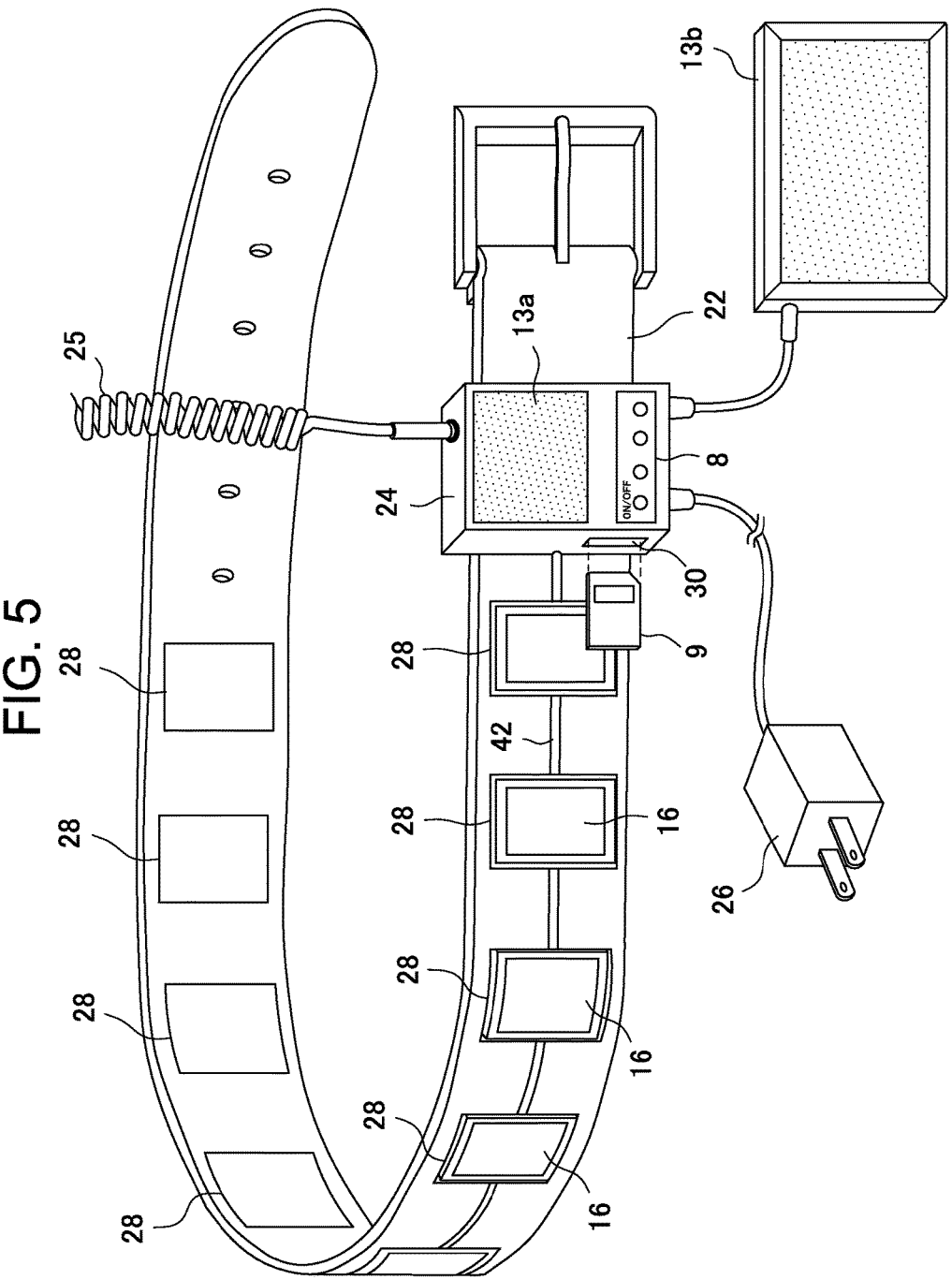
FIG. 5 is an explanatory diagram showing a control unit of a medical image recording device of an embodiment of the present invention.

As shown in FIGS. 4 and 5, the operator wraps a battery holding belt 22 around his/her waist; a battery power source is held by the battery holding belt 22 as an operation power source for this medical image recording device. The battery power source includes a plurality of rechargeable batteries 16, which are connected to each other. The battery holding belt 22 includes mounting sections 28 into which the batteries 16 are inserted in a detachable manner. On the battery holding belt 22, a control unit 24 is mounted along with the batteries 16. The batteries 16 are connected to the control unit 24.

On the surface of a unit casing of the control unit 24, the operation unit 8 and the display panel 13*a* of the display unit 13, which is a liquid crystal panel or an organic EL panel, are disposed. The display panel 13*a* is used as a monitor screen for captured images. Another display panel 13*b* is provided so that nearby people, such as treatment assistants, can monitor how the treatment is going on. In this case, if signals of the image data are transmitted wirelessly from the control unit 24 to the display panel 13*a*, the operator can move freely during the treatment.

If a Wi-Fi network camera is used as the image pickup device 1, the video can be fed to a terminal device with a display panel 13*b* via the internet so that the monitoring is possible. In this case, in the terminal device, the URL of the network camera is specified on a WEB browser. Therefore, the terminal device can take in the images captured by the network camera of how the treatment is being carried out via the internet in real time. In this manner, the upside of using a wireless LAN is that the treatment can be monitored in real time through terminal devices at any locations other than where the treatment is carried out.

On a side surface of the unit casing, a slot 30, into which the memory card 9 is inserted in a detachable manner, is formed. A control board on which the CPU 10, the ROM 11, the RAM 12, the signal processing unit 7, and the display unit 13 are mounted is housed inside the unit casing.

A cable harness 25 is a bundle of: a power cord, which supplies drive current from the control unit 24 to the image pickup device 1 and the illumination unit 15; signal lines of control signals, which are output from the CPU 10 to the image pickup element displacement mechanism 5 and the lens adjustment mechanism 6; and an input signal line, which extends from the acceleration sensor 4 to the CPU 10.

If a charger 26 whose plug is plugged into an electrical outlet 27 is connected to the control unit 24, the image pickup device 1 and the illumination unit 15 can be used to carry out a shooting operation and an illumination operation when the batteries 16 are being charged. Therefore, the video can be shot even during a prolonged treatment.

The operation of the above medical image recording device will be described. When the operation unit 8 of the control unit 24 is operated to turn the medical image recording device ON, the CPU 10 loads the control programs onto the ROM 11 to initiate the operation of the medical image recording device. At this time, if the operator directs his/her face at a subject or a treatment target location, the image pickup control unit 10*a* carries out an auto focus process and an exposure adjustment process for the subject. When a zooming switch of the operation unit 8 is operated, the image pickup control unit 10*a* adjusts the zooming of the optical lens 2. The illumination control unit 10*g* controls the illumination drive unit 14 and turns the illumination unit 15 ON by supplying drive current to the illumination unit 15 in such a way that a normal level of brightness is secured.

When the release switch of the operation unit 8 is operated, the image pickup control unit 10*a* starts to shoot a video. The image pickup control unit 10*a* sequentially takes in image data of each frame from the signal processing unit 7 to store the image data in the RAM 12, and carries out image processing, such as white balance adjustment, color interpolation processing, and aberration correction processing, on the stored image data. Then, the image pickup control unit 10*a* sequentially reads the image data that is stored in the RAM 12 and has undergone the image processing, and outputs the image data to the display unit 13. The video is displayed on the display unit 13 as a result. As described above, the signal processing unit 7's function to sequentially generate the image data of each frame may be realized by the CPU 10 that executes the control programs of the ROM 11.

The compression and decompression processing unit 10*d* compresses the image data in JPEG after the image data, stored in the RAM 12, underwent the image processing. The compressed image data is transmitted to the memory card 9 and recorded in an image file of the video.

FIGS. 7A and 8A schematically show images of image data whose each frame is taken into the image pickup control unit 10*a* from the signal processing unit 7, when image signals of images taken by the image pickup device 1 that is put on the head via the above binocular loupe 20 or headband 21 are output to the signal processing unit 7 during treatment by the operator. The image pickup control unit 10*a* actually takes in the image data at a rate of 30 frames per second, in order to shoot a video via the image pickup device 1. For ease of explanation, in the case of FIGS. 7A and 8A, a series of images during the treatment is simplified in such a way as to only show images of representative frames.

The image pickup control unit 10*a* takes in the image data of each frame from the signal processing unit 7, and stores the image data in the RAM 12 without any change. The image pickup control unit 10*a* then carries out image processing, such as white balance adjustment, color interpolation processing, and aberration correction processing. Then, the image pickup control unit 10*a* sequentially reads the image data that is stored in the RAM 12 and has undergone the image processing, and outputs the image data to the display unit 13. The video is displayed on the display unit 13 as a result.

The compression and decompression processing unit 10d compresses, in JPEG, each set of the image data sequentially stored in the RAM 12. The compressed image data is transmitted to the memory card 9 and recorded in an image file. FIGS. 7A and 8B schematically show the image data recorded on the memory card 9.

The operation will be described with the use of FIGS. 7 and 8. The subject recognition unit 101b recognizes a main subject from image data of each frame that the image pickup control unit 10a sequentially receives from the signal processing unit 7. In the second movement detection unit of the movement detection unit 10b, the subject recognition unit 101b sequentially analyzes each of recognized images between frames that are adjacent to each other at intervals of 1/30 seconds, or each of recognized images between, frames that are close to each other, for example, at intervals of 1/3 seconds, in order to calculate a positional shift of the main subject. If the main subject does not change significantly between frames being analyzed, or if the calculated positional-shift value does not exceed the threshold value, it is determined, that the image pickup device 1 keeps shooting the same subject. To be more precise, the main subject is gradually changing as the treatment proceeds. Therefore, at the time when the image F3 appears, the movement detection unit 10b recognizes an organ exposed by opening of the abdomen as a main subject, which is significantly different from the main subject recognized when the image F1 appears.

At this time, for example, suppose that the operator suspends the treatment and turns his/her face to an assistant to give the treatment assistant instructions. At this time, the image pickup device 1 takes an image of the assistant, and the image pickup control unit 10a takes in a frame of image F4 from the signal processing unit 7. When the subject has abruptly changed in this manner, there is a great shift from the main subject that the movement detection unit 10b has so far recognized by sequentially carrying out pattern matching between the frames. If there is a great shift from the main subject, the positional-shift value calculated exceeds a present threshold value. Accordingly, the movement detection unit 10b judges that the shooting direction of the image pickup device 1 has moved away from the subject (treatment target location).

As a result, the recording control unit 10e prohibits the compression and decompression processing unit 10d from writing the compressed image data to the memory card 9. Therefore, the image F4 of FIG. 7A is not recorded on the memory card 9 as shown in FIG. 7B. The image pickup control unit 10a continues the process of storing the image data of each frame coming from the signal processing unit 7 in the RAM 12, as well as the image processing, such as white balance adjustment, on the stored image data. Therefore, even if the treatment is suspended, the image taken by the image pickup device 1 will be displayed on the display unit 13 and can be monitored. However, when the movement detection unit 10b judges that the shooting direction of the image pickup device 1 has moved away from the treatment target location, the image pickup control unit 10a stops the process of storing the image data of each frame coming from the signal processing unit 7 in the RAM 12, as well as the image processing, such as white balance adjustment, on the stored image data. During a period in which the image pickup device 1 is shooting any location other than where the treatment is carried out, the image pickup control unit 10a may display, as a still image, a previously captured image F3 of the treatment target location taken by the image pickup device 1 on the display unit 13.

When the movement detection unit 10b judges that the shooting direction of the image pickup device 1 has moved away from the treatment target location, the illumination control unit 10g controls the illumination drive unit 14 to halt the supply of power to the illumination unit 15 or reduce the current supplied to the illumination unit 15, thereby preventing the batteries 16 from being consumed.

Even after a drastic change of the main subject caused by the suspension of the treatment, the movement detection unit 10b uses the subject recognition unit 101b to keep recognizing the main subject by carrying out a pattern matching process of image data of each frame that the image pickup control unit 10a receives from the signal processing unit 7, and makes a determination as to whether the recognized main subject resembles a previous main subject (i.e. treatment target location), which is captured before the positional-shift value exceeds the threshold value. If the movement detection unit 10b detects that the main subject recognized by the subject recognition unit 101b resembles the previous main subject, then the movement detection unit 10b judges that the operator has restarted the treatment. As a result, the image F5 and other images that come after the restart of the treatment are compressed by the compression and decompression processing unit 10d. The compressed image data are sequentially recorded on the memory card 9 by the recording control unit 10e. In this manner, on the memory card 9, only image files of video of how the operator is conducting the treatment are recorded. The illumination control unit 10g controls the illumination drive unit 14 to restart the supply of power to the illumination unit 15 or bring the amount of current supplied to the illumination unit 15 back to a normal level.

This embodiment, too, has a time-lag period of 0.2 to 0.5 seconds, for example, as described above. If the operator does not have any intention to suspend the operation but the operator temporarily turns his/her face away from the treatment target location before immediately moving the face back to the treatment target location, an image of a location other than where the treatment is being carried out may be taken by the image pickup device 1 during that short period of time and be displayed on the display unit 13. In such a case, the time-lag period can prevent the images from being displayed unnaturally. The recording control unit 10e may wait for the time-lag period to pass before controlling the stop of writing of image data to the memory card 9; the illumination control unit 10g may wait for the time-lag period to pass before controlling in such a way as to stop the supply of power to the illumination unit 15 or reduce the current supplied to the illumination unit 15.

When the operator directs his/her face at a ceiling light during the treatment, then the image pickup device 1 takes image F6 (FIG. 8A). The image F6 is stored in the RAM 12 by the image pickup control unit 10a. However, the recording control unit 10e does not record the image F6 on the memory card 9 (FIG. 8B). Similarly, the illumination control unit 10g controls the illumination unit 15 in such a way as to turn the illumination unit 15 OFF or lower the illumination intensity.

When the operator turns his/her eyes back to the treatment target location, the image F7 that the image pickup control unit 10a receives from the signal processing unit 7 includes the same main subject as the image F5 does. Therefore, the compressed data of the image F7 is recorded on the memory card 9, and is displayed on the display unit 13, and the illumination control unit 10g brings the illumination unit 15 back to normal conditions.

If the acceleration sensor 4 detects the movement of the head of the operator during the shooting of the video, the first movement detection unit of the movement detection unit 10b calculates, from angular velocities of X, Y, and Z that are output from the acceleration sensor 4, the amounts of movement of the image pickup device 1 in the left-right direction (X-direction), the up-down direction (Y-direction), and the front-back direction (Z-direction). In an edge portion of a detection signal supplied from the acceleration sensor 4, distortion, such as ringing or overshooting/undershooting, occurs. Accordingly, the movement detection unit 10b takes into account in advance a period during which the distortion will attenuate in the edge portion of the detection signal supplied from the acceleration sensor 4, in setting a delay time; the movement detection unit 10b therefore calculates the amounts of movement of the image pickup device 1 after the delay time has passed.

Then, the movement detection unit 10b determines whether the values of the amounts of movement calculated are less than or equal to a preset shake judgment threshold value. The shake judgment threshold value is a criterion for determining whether a blur detected by the acceleration sensor 4 is a degree of movement that is unlikely to affect, the qualify of the captured images. If the values of the amounts of movement calculated exceed the shake judgment threshold value, the movement detection unit 10b then judges that a "camera shake" has occurred.

If the movement detection unit 10b judges that a "camera shake" has occurred, the movement detection unit 10b controls the image pickup element displacement mechanism 5 to move, based on the amounts of movement calculated at that time, the image pickup element 3 in a direction of cancelling the blur. For example, when the image pickup device 1 is causing a blur in the right direction, the camera shake correction unit 10c controls the image pickup element displacement mechanism 5 to move the image pickup element 3 in the left direction by an amount equivalent to the amount of movement. Therefore, the signal processing unit 7 can generate the same image data as when no "camera shake" has occurred. Accordingly, in the image data of each frame that the signal processing unit 7 outputs to the image pickup control unit 10a, a "camera, shake" has been corrected. Incidentally, if a "camera shake" is to be mechanically corrected, a correction lens is incorporated into the optical lens 2, and the correction lens is moved by the same amount that the image pickup device 1 has moved in a direction of cancelling the blur. In this manner, a camera shake correction mechanism that corrects an optical axis may be used.

In that manner, if the amount of movement that the movement detection unit 10b calculates from a detection signal supplied from the acceleration sensor 4 exceeds the threshold value, which is used to determine whether a "camera shake" has occurred, the camera shake correction unit 10c makes a correction, and the image pickup control unit 10a displays, on the display unit 13, an image of image data that is stored in the Ram 12 and has undergone the image processing, such as white balance adjustment.

In that manner, if the movement detection unit 10b (first movement detection unit) detects a "camera shake" with the acceleration sensor 4, the camera shake correction unit 10c corrects the camera shake, and the image pickup control unit 10a displays, on the display unit 13, the images of the image data that are stored in the RAM 12 and have undergone the image processing, such as white balance adjustment. If the movement detection unit 10b (second movement detection unit) detects a shift in the shooting of the image pickup device 1 away from the treatment target location by using the subject recognition unit 101b, the recording control unit 10e does not record the image data of images at that time on the memory card 9. On the memory card 9, only the video of how the operator is conducting the treatment is recorded. Therefore, only the video of how the operator is conducting the treatment is recorded on the memory card 9. Thus, the video is highly effective as a record of the treatment.

Second Embodiment

According to the second embodiment, the amount of movement is electronically detected without the use of the acceleration sensor 4 in order to correct a "camera shake", and a shift in the shooting direction of the image pickup device 1 away from a subject (treatment target location) is detected. Then, the "camera shake" is electronically corrected without the use of the image pickup element displacement mechanism 5.

Figure 6:
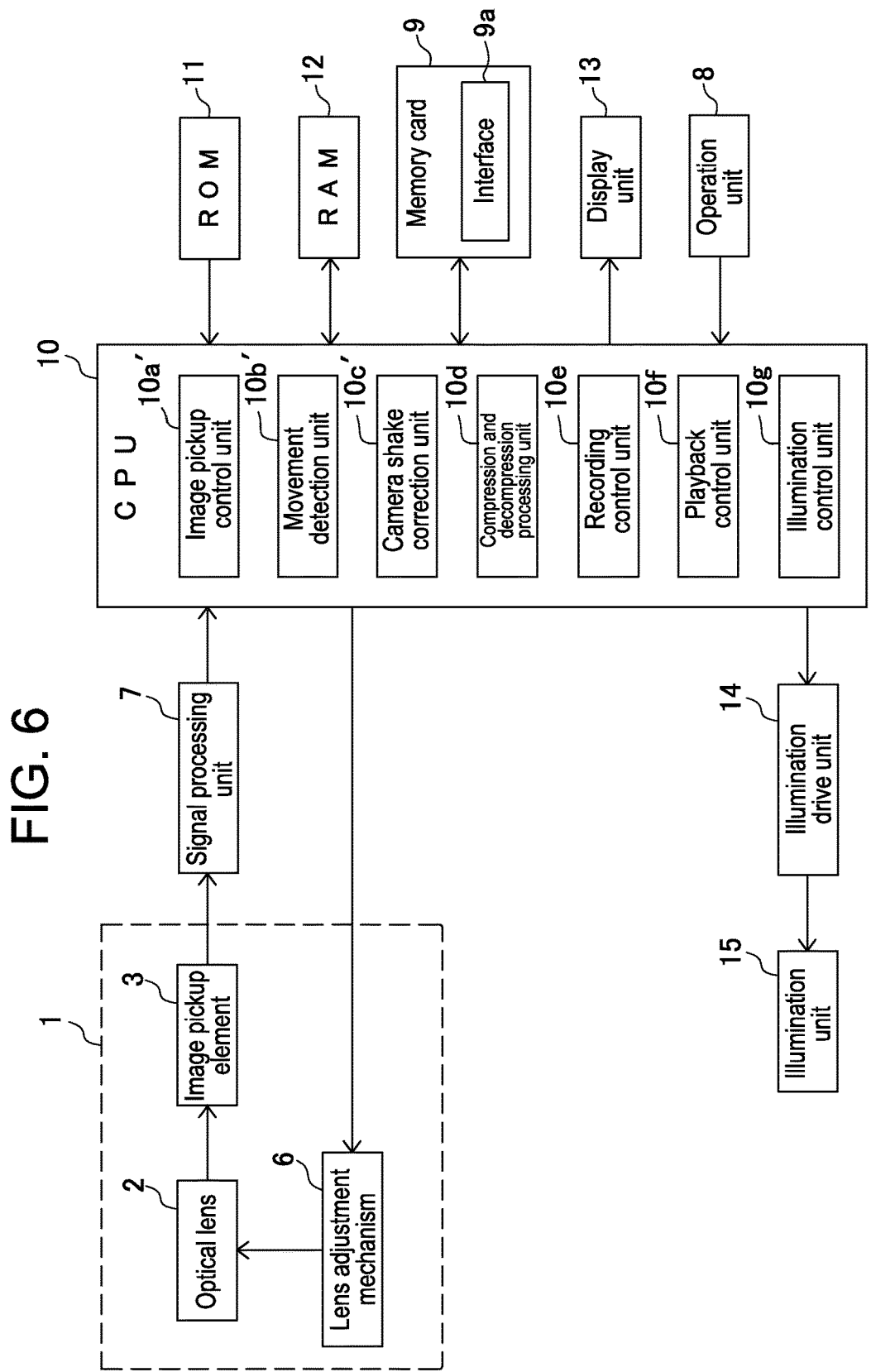
FIG. 6 is a diagram showing, as blocks, electric circuits of a medical image recording device according to a second embodiment of the present invention.

FIG. 6 is a block diagram showing the schematic configuration of a medical image recording device according to the second embodiment. This configuration is the same as the embodiment shown in FIG. 1 except that the acceleration sensor 4 and the image pickup element displacement mechanism 5 do not exist. However, since the acceleration sensor 4 and the image pickup element displacement mechanism 5 do not exist, the configuration of the control programs stored in the ROM 11 that are executed by the CPU 10 is partially altered. A movement detection unit 10b' and a camera shake correction unit 10c' in the CPU 10 of FIG. 6 carry out control described below.

That is, the movement detection unit 10b' carries out control in such a way as to calculate an amount of movement of the image pickup device 1 based on an amount of positional shift of a main subject captured by each of images between frames that are adjacent to each other at intervals of 1/30 seconds, or an amount of positional shift of the main subject in a positional-shift image of the main subject captured by each of images between frames that are close to each other, for example, at intervals of 1/3 seconds.

If the amount of movement calculated by the movement detection unit 10b' exceeds a threshold value that is used to identify a "camera shake", the camera shake correction unit 10c' generates a synthetic image from images of two consecutive or adjacent frames, and controls in such a way as to output the image data.

In addition to the control described on the image pickup control unit 10a, the image pickup control unit 10a' carries out additional control in such a way as to store the synthetic image data, in which the "camera shake" has been corrected, in the RAM 12.

The operation of the medical image recording device of FIG. 6 will be described. When the release switch of the operation unit 8 is operated, the image pickup control unit 10a' starts to shoot a video. The image pickup control unit 10a' sequentially takes in image data of each frame from the signal processing unit 7.

FIGS. 9A and 10A schematically show images of each frame that is taken into the image pickup control unit 10a' from the signal processing unit 7, when images taken by the image pickup device 1 that is put on the head via the above binocular loupe 20 or headband 21 are output to the signal processing unit 7 during treatment by the operator. The signal processing unit 7 actually generates the image data at a rate of 30 frames per second in order to allow the image pickup device 1 to shoot a video. For ease of explanation, a series of images during the treatment is simplified in such a way as to only show images of representative frames.

As in the case of the subject recognition unit 101b described in FIG. 1, the movement detection unit 10b' uses a pattern matching method to analyze the images between previous and subsequent frames of each set of image data of each frame that the image pickup control unit 10a takes in. Then, the movement detection unit 10b' extracts the contours of the subject as feature points, and recognizes an area where the feature points overlap with one another as a main subject.

The movement detection unit 10b' calculates an amount of a positional shift in the vertical and horizontal directions on X-Y axes of the main subject in each of the images between frames that are adjacent to each other or in each of the images between frames that are close to each other. The movement detection unit 10b' determines whether the calculated positional-shift amount (or the amount of movement of the image pickup device 1) is within a preset range. The lower limit of the range is a threshold value at which the positional shift of the subject does not seem to cause a blur and is judged to be a degree of movement that is unlikely to affect the quality of the captured images; the upper limit of the range is a threshold value at which it is determined that the shooting direction of the image pickup device 1 has significantly moved away from the subject (treatment target location). When the value of the amount of movement calculated is within the preset range, the movement detection unit 10b' judges that a "camera shake" has occurred. This range will be referred to as "camera shake detection range" in the description of this embodiment.

Image F1' of a pre-treatment state, which is shown as a representative image in FIG. 9A, image F2', which shows a process of opening the abdomen, and image F3', which comes after the opening of the abdomen, are significantly different. However, the movement detection unit 10b' sequentially analyzes images between frames that are adjacent to each other at intervals of 1/30 seconds during that period, or images between frames that are close to each other, for example, at intervals of 1/3 seconds, and there are no significant differences between the previous and subsequent frames. Therefore, the movement detection unit 10b' judges that the image pickup device 1 keeps shooting the same subject. That is, since the calculated positional-shift value is less than or equal to the upper limit of the "camera shake detection range", the movement detection unit 10b' judges that the image pickup device 1 keeps shooting the same subject.

During a period in which the movement detection unit 10b' judges that the image pickup device 1 keeps shooting the treatment target location, the image pickup control unit 10a' stores the image data of all frames during that period, including images F1' to F3', in the RAM 12 without any change, and carries out image processing, such as white balance adjustment, color interpolation processing, and aberration correction processing. Then, the image pickup control unit 10a' sequentially reads the image data that is stored in the RAM 12 and has undergone the image processing, and outputs the image data to the display unit 13. The video is displayed on the display unit 13 as a result. FIGS. 9B and 10B schematically shows the image data of each frame stored in the RAM 12.

The compression and decompression processing unit 10d compresses, in JPEG, each set of the image data sequentially stored in the RAM 12. The compressed image data is transmitted to the memory card 9 and recorded. FIGS. 9C and 10C schematically show the image data recorded on the memory card 9.

When the movement detection unit 10b' analyzes the images between the frames and extracts the contours of a subject as feature points, the movement detection unit 10b' calculates the amount of movement of the image pickup device 1 from an amount of positional shift on coordinate axes of a main subject in both images. Then, if the amount of movement is within the "camera shake detection range", the movement detection unit 10b' judges that a "camera shake" has occurred.

Suppose that the images F3' and F4' in FIG. 9A are images of consecutive frames. In this case, the main subject has moved in the horizontal (X-axis) direction, and the value of the amount of movement of the image pickup device 1 calculated by the movement detection unit 10b' is within the "camera shake detection range". Therefore, the movement is judged to be a "camera shake". At this time, the camera shake correction unit 10c' generates a superimposed synthetic image F4A by calculating the averages of coordinates of the main subject in the images F3' and F4'.

If the movement detection unit 10b' detects an image shift, then the image pickup control unit 10a' stores the synthetic image F4A, which is created by the camera shake correction unit 10c, in the RAM 12 (FIG. 9B), carries out image processing, such as white balance adjustment, color interpolation processing, and aberration correction processing, and outputs the image data of the synthetic image F4A, which has undergone the image processing, to the display unit 13. The compression and decompression processing unit 10d compresses, in JPEG, the image data of the synthetic image F4A. The compressed image data is transmitted to the memory card 9 and is recorded (FIG. 9C). In that manner, in the case of the third embodiment, the image pickup element displacement mechanism 5 is not used to optically correct the "camera shake". Accordingly, the image F4' on which the "camera shake" has occurred is corrected into the image F4A before being displayed on the display unit 13 and recorded on the memory card 9.

For example, if the operator suspends the treatment and turns his/her face to an assistant to give the treatment assistant instructions during the shooting by the image pickup device 1, then the image pickup device 1 takes an image of the assistant, and the image pickup control unit 10a' takes in the image data of image F5' from the signal processing unit 7. In such a case, the main subject is different from the one identified in the previous frame. Therefore, when the movement detection unit 10b' detects an image shift between frames by carrying out pattern matching, the value of the amount of movement of the image pickup device 1 calculated from the shift is greater than the upper limit of the "camera shake detection range". As a result, the movement detection unit 10b' judges that the shooting direction of the image pickup device 1 has moved from the subject.

The camera shake correction unit 10c' does not carry out a process of generating a synthetic image of images of both frames when the amount of movement of the image pickup device 1 is greater than the upper limit of the "camera shake detection range". However, the image pickup control unit 10a' stores the image data in the RAM 12 without any change (FIG. 9B), and reads the image data to display on the display unit 13 after conducting image processing, such as white balance adjustment, color interpolation processing, and aberration correction processing; or the image pickup control unit 10a' may stop the real-time displaying of the images captured by the image pickup device 1, and instead display, as a still image, a previously captured image F4A of the treatment target location taken by the image pickup device 1 on the display unit 13.

When the amount of movement of the image pickup device 1 is greater than the upper limit of the "camera shake detection range", the recording control unit 10e' prohibits the frames that follow from being written to the memory card 9 (FIG. 9C). The illumination control unit 10g controls the illumination drive unit 14 to halt the supply of power to the illumination unit 15 or reduce the current supplied to the illumination unit 15.

Even after judging that the shooting direction of the image pickup device 1 has changed given that the amount of movement has exceeded the upper limit of the "camera shake detection range", the movement detection unit 10b' continues the pattern matching process of image data of each frame that the image pickup control unit 10a' receives from the signal processing unit 7, and makes a determination as to whether the image data resembles that of a main subject (i.e. treatment target location) that appears before the amount of movement exceeds the upper limit of the "camera shake detection range". If the movement detection unit 10b detects that a main subject recognized by the subject recognition unit 101b resembles a main subject that appears before the shooting direction of the image pickup device 1 moves, then the movement detection unit 10b judges that the operator has resumed the treatment. Accordingly, the image F6' and other images that come after the resumption of the treatment are compressed by the compression and decompression processing unit 10d. The compressed image data are sequentially recorded on the memory card 9 by the recording control unit 10e (FIG. 10C). The illumination control unit 10g controls the illumination drive unit 14 to resume the supply of power to the illumination unit 15 or bring the amount of current supplied to the illumination unit 15 back to a normal level.

This embodiment, too, has a time-lag period of 0.2 to 0.5 seconds, for example, as described above. As a result, if the operator temporarily turns his/her face away from the treatment target location before immediately moving the face back to the treatment target location, an image taken by the image pickup device 1 of a location other than where the treatment is being carried out may not be displayed on the display unit 13. The recording control unit 10e may wait for the time-lag period to pass before controlling the stop of writing of image data to the memory card 9; the illumination control unit 10g may wait for the time-lag period to pass before controlling in such a way as to stop the supply of power to the illumination unit 15 or reduce the current supplied to the illumination unit 15.

When the operator turns his/her face at a ceiling light during the treatment, then the image pickup device 1 takes image F7' (FIG. 10A). The image F7' is stored in the RAM 12 by the image pickup control unit 10a' (FIG. 10B). However, the recording control unit 10e does not record the image F7' on the memory card 9 (FIG. 10C). When the operator turns his/her eyes back to the subject, the image F8' that the image pickup device 1 outputs includes the same main subject as the image F6' does. Therefore, the compressed data of the image F6 is recorded on the memory card 9.

In the image F9' of a frame that follows the image F8', the position of the main subject has moved in the up-down (Y-direction) compared with the image F8'. The movement detection unit 10b detects an image shift, and judges that a "camera shake" has occurred if the value of the amount of movement of the image pickup device 1 calculated from the shift is within the "camera shake detection range". At this time, the camera shake correction unit 10c generates a superimposed synthetic image F9A by calculating the averages of coordinates of the main subject in the images F8' and F9'. The image data of the synthetic image F9A is stored in the RAM 12 (FIG. 10B), and the compressed image data thereof is recorded on the memory card 9 (FIG. 10C).

In this manner, as for the image data of frames between the image 9' and the image F10', when the movement detection unit 10b' is not detecting a "camera shake", the images of image data that are stored in the RAM 12 by the image pickup control unit 10a' and have undergone the image processing such as white balance adjustment are displayed on the display unit 13. If a "camera shake" is detected, the image data of a synthetic image generated from the image data of previous and subsequent frames undergoes the image processing, and is stored in the RAM 12 and displayed on the display unit 13.

The image data of an image that does not cover a main subject by the movement detection unit 10b' is not recorded on the memory card 9. Therefore, only the video of how the operator is conducting the treatment is recorded on the memory card 9. Thus, the video is highly effective as a record of the treatment.

The medical image recording device of that embodiment detects a "camera shake" based on an image shift of two consecutive or adjacent frames of video. Therefore, the medical image recording device can suppress the "camera shake". When the shooting of the image pickup device 1 has significantly deviated from the subject (treatment target location), the recording of captured images of that portion is stopped. Therefore, only valid recorded video can be saved.

While the present invention has been described in detail, the present invention is not limited to the above embodiments. Various modifications may be made based on the spirit of the present invention, and those modifications will not be excluded from the scope of the present invention.

INDUSTRIAL APPLICABILITY

The present invention relates to a medical image recording device that shoots progress of treatment by using an image pickup device put on the body of an operator and which is able to leave, as a record, only a series of images directly related to the treatment. The present invention has industrial applicability.

EXPLANATION OF REFERENCE SYMBOLS

1: Image pickup device
2: Optical lens
3: Image pickup element
4: Acceleration sensor
7: Signal processing unit
9: Memory card (information recording unit)
10: CPU
10a, 10a': Image pickup control unit
10b, 10b': Movement detection unit
10c, 10c': Camera shake correction unit
10e: Recording control unit
15: Illumination unit

The invention claimed is:

1. A medical image recording device that shoots by putting, on a body of an operator conducting medical treatment, an image pickup device that includes at least an optical lens and an image pickup element which generates an image pickup signal by photoelectrically converting light introduced from a subject via the optical lens during shooting, the medical image recording device comprising:

an image pickup control unit that controls in such a way as to display, on a display unit, a video from image data that is generated for each of frames that constitute the video based on the image pickup signal;

an information recording unit that sequentially records the image data;

a movement detection unit that sequentially compares the image data between consecutive or adjacent frames, and calculates an amount of movement of the image pickup device based on a positional shift of a main subject between the frames;

a camera shake correction unit that corrects, when the amount of movement is within a preset range, a positional shift of the video caused by the movement corresponding to the amount of movement; and a recording control unit that controls stopping of the recording of the image data on the information recording unit when the amount of movement is greater than an upper limit of the range, wherein the image pickup control unit stops the displaying of the video when the amount of movement is greater than the upper limit of the range and the image pickup control unit controls in such a way as to display, as a still image, the image data of the frame that appears immediately before the amount of movement exceeds the upper limit of the range, after the displaying of the video is stopped.

2. The medical image recording device according to claim 1, wherein the recording control unit controls resumption of recording of the image data by the information recording unit after the amount of movement exceeds the upper limit of the range and after a main subject detected by the movement detection unit comes to resemble the main subject that appears immediately before the amount of movement exceeds the upper limit of the range.

3. The medical image recording device according to claim 2, wherein the image pickup control unit controls resumption of displaying of the video after the amount of movement exceeds the upper limit of the range and after a main subject detected by the movement detection unit comes to resemble the main subject that appears immediately before the amount of movement exceeds the upper limit of the range.

4. A medical image recording device that shoots by putting, on a body of an operator conducting medical treatment, an image pickup device that includes at least an optical lens and an image pickup element which generates an image pickup signal by photoelectrically converting light introduced from a subject via the optical lens during shooting, the medical image recording device comprising:

an image pickup control unit that controls in such a way as to display, on a display unit, a video from image data that is generated for each of frames that constitute the video based on the image pickup signal;

an information recording unit that sequentially records the image data;

a movement detection unit that sequentially compares the image data between consecutive or adjacent frames, and calculates an amount of movement of the image pickup device based on a positional shift of a main subject between the frames;

a camera shake correction unit that corrects, when the amount of movement is within a preset range, a positional shift of the video caused by the movement corresponding to the amount of movement;

a recording control unit that controls stopping of the recording of the image data on the information recording unit when the amount of movement is greater than an upper limit of the range; and an illumination unit that emits light to the subject, wherein, when the amount of movement is greater than the upper limit of the range, the illumination unit stops the emission of the light or lowers the illumination intensity.

5. The medical image recording device according to claim 4, wherein the illumination unit stops the emission of the light or lowers the illumination intensity after a predetermined time-lag period has passed since the movement detection unit detects that the amount of movement exceeds the upper limit of the range.

6. The medical image recording device according to claim 4, wherein the illumination unit resumes the emission of the light or increases the illumination intensity after the amount of movement exceeds the upper limit of the range and after a main subject detected by the movement detection unit comes to resemble the main subject that appears immediately before the amount of movement exceeds the upper limit of the range.

7. A medical image recording device that shoots by putting, on a body of an operator conducting medical treatment, an image pickup device that includes at least an optical lens and an image pickup element which generates an image pickup signal by photoelectrically converting light introduced from a subject via the optical lens during shooting, the medical image recording device comprising:

an image pickup control unit that controls in such a way as to display, on a display unit, a video from image data that is generated for each of frames that constitute the video based on the image pickup signal;

an information recording unit that sequentially records the image data;

an acceleration sensor that detects movement of the image pickup device;

a first movement detection unit that calculates an amount of movement of the image pickup device based a detection signal of the acceleration sensor;

a camera shake correction unit that controls in such a way as to cancel a blur in the video caused by the movement corresponding to the amount of movement calculated by the first movement detection unit;

a second movement detection unit that sequentially compares the image data between consecutive or adjacent frames, and calculates an amount of movement of the image pickup device from a positional shift of a main subject between the frames; and a recording control unit that controls stopping of the recording of the image data when the amount of movement calculated by the second movement detection unit is greater than or equal to a preset threshold value.

8. The medical image recording device according to claim 7, wherein the first movement detection unit takes into account in advance a period during which distortion attenuates in an edge portion of a detection signal of the acceleration sensor, in setting a delay time, and calculates the amount of movement after the delay time has passed.

9. The medical image recording device according to claim 7, wherein
the image pickup control unit stops, when the amount of movement calculated by the second movement detection unit is greater than or equal to the threshold value, the displaying of the video.

10. The medical image recording device according to claim 9, wherein
the image pickup control unit stops the displaying of the video after a predetermined time-lag period has passed since detecting that the amount of movement calculated by the second movement detection unit is greater than or equal to the threshold value.

11. The medical image recording device according to claim 9, wherein
the image pickup control unit displays, as a still image, the image data that appears immediately before the amount of movement calculated by the second movement detection unit becomes greater than or equal to the threshold value, after the displaying of the video is stopped.

12. The medical image recording device according to claim 9, wherein
the image pickup control unit controls resumption of displaying of the video after the amount of movement calculated by the second movement detection unit becomes greater than or equal to the threshold value and after a main subject detected by the second movement detection unit comes to resemble the main subject that appears immediately before the amount of movement exceeds the threshold value.

13. The medical image recording device according to claim 7, wherein
the recording control unit controls resumption of recording of the image data by the information recording unit after the amount of movement calculated by the second movement detection unit becomes greater than or equal to the threshold value and after a main subject detected by the second movement detection unit comes to resemble the main subject that appears immediately before the amount of movement exceeds the threshold value.

14. The medical image recording device according to claim 7, comprising
an illumination unit that emits light to the subject, wherein, when the amount of movement calculated by the second movement detection unit becomes greater than or equal to the threshold value, the illumination unit stops the emission of the light or lowers the illumination intensity.

15. The medical image recording device according to claim 14, wherein
the illumination unit resumes the emission of the light or increases the illumination intensity after the amount of movement calculated by the second movement detection unit exceeds the threshold value and after a main subject detected by the second movement detection unit comes to resemble the main subject that appears immediately before the amount of movement exceeds the threshold value.

* * * * *